United States Patent
Guillama et al.

(10) Patent No.: US 10,416,839 B2
(45) Date of Patent: Sep. 17, 2019

(54) DECISION-ORIENTED HEXAGONAL ARRAY GRAPHIC USER INTERFACE

(71) Applicant: SynaBEE, Inc., Wellington, FL (US)

(72) Inventors: Noel J. Guillama, Wellington, FL (US); Chester A. Heath, Boca Raton, FL (US); Jahziel M. Guillama, Wellington, FL (US); Carl L. Larsen, West Palm Beach, FL (US)

(73) Assignees: SYNABEE, INC., Wellington, FL (US); THE QUANTUM GROUP, INC., Lake Worth, FL (US); Noel J. Guilliama, Wellington, FL (US)

( * ) Notice: Subject to any disclaimer, the term of this patent is extended or adjusted under 35 U.S.C. 154(b) by 426 days.

(21) Appl. No.: 14/434,977

(22) PCT Filed: Oct. 8, 2013

(86) PCT No.: PCT/US2013/063777
§ 371 (c)(1),
(2) Date: Apr. 10, 2015

(87) PCT Pub. No.: WO2014/058816
PCT Pub. Date: Apr. 17, 2014

(65) Prior Publication Data
US 2015/0261412 A1 Sep. 17, 2015

Related U.S. Application Data
(60) Provisional application No. 61/711,895, filed on Oct. 10, 2012.

(51) Int. Cl.
*G06F 3/0481* (2013.01)
*G06F 3/0482* (2013.01)
(Continued)

(52) U.S. Cl.
CPC ........ *G06F 3/04817* (2013.01); *G06F 3/0482* (2013.01); *G06F 3/0488* (2013.01); *G06F 3/04842* (2013.01); *G16H 40/63* (2018.01)

(58) Field of Classification Search
CPC ....... G06F 2203/04806; G06F 3/04815; G06F 3/0482; G06F 3/0485; G06F 3/0488; G06F 3/04886
See application file for complete search history.

(56) References Cited

U.S. PATENT DOCUMENTS

| | | | |
|---|---|---|---|
| 2003/0064757 A1* | 4/2003 | Yamadera | G06F 3/0482 455/566 |
| 2004/0150668 A1* | 8/2004 | Myers | G06F 3/0421 715/771 |

(Continued)

FOREIGN PATENT DOCUMENTS

| | | | |
|---|---|---|---|
| EP | 1921575 A1 * | 5/2008 | ............. G06Q 10/06 |
| EP | 1921575 A1 | 5/2008 | |

OTHER PUBLICATIONS

International Search Report from PCTIUS 2013/063777 dated Jan. 23, 2014.

*Primary Examiner* — Sang H Kim
(74) *Attorney, Agent, or Firm* — Nixon Peabody LLP; Anthony M. Duncan, Jr.

(57) ABSTRACT

A hexagonal graphical user interface (GUI) is provided in which a user interface is rendered including one or more primary icons, each of the one or more primary icons comprising a hexagon and representing an initial state. In the GUI, responsive to the selection of a first icon from the primary icons, one or more secondary icons are displayed, where each of the secondary icons is a hexagon and positioned in the user interface in a hexagonal tiling (hextile) arrangement with respect to at least one of the first icon or another one of the secondary icons, and where each of the
(Continued)

secondary icons represents additional states subsequent to the initial state along valid paths from the initial state.

17 Claims, 18 Drawing Sheets

(51) Int. Cl.
*G06F 3/0484* (2013.01)
*G06F 3/0488* (2013.01)
*G16H 40/63* (2018.01)

(56) References Cited

U.S. PATENT DOCUMENTS

| | | |
|---|---|---|
| 2005/0035964 A1* | 2/2005 | Heenan .................... G06T 17/20 345/420 |
| 2011/0047491 A1* | 2/2011 | Hwang ................. G06F 3/0488 715/765 |
| 2012/0005622 A1 | 1/2012 | Park et al. |
| 2013/0117280 A1* | 5/2013 | Donaldson ............ G06F 16/904 707/748 |
| 2013/0311954 A1* | 11/2013 | Minkkinen ......... G06F 3/04812 715/862 |
| 2015/0128049 A1* | 5/2015 | Block ................... G06F 3/1423 715/728 |

* cited by examiner

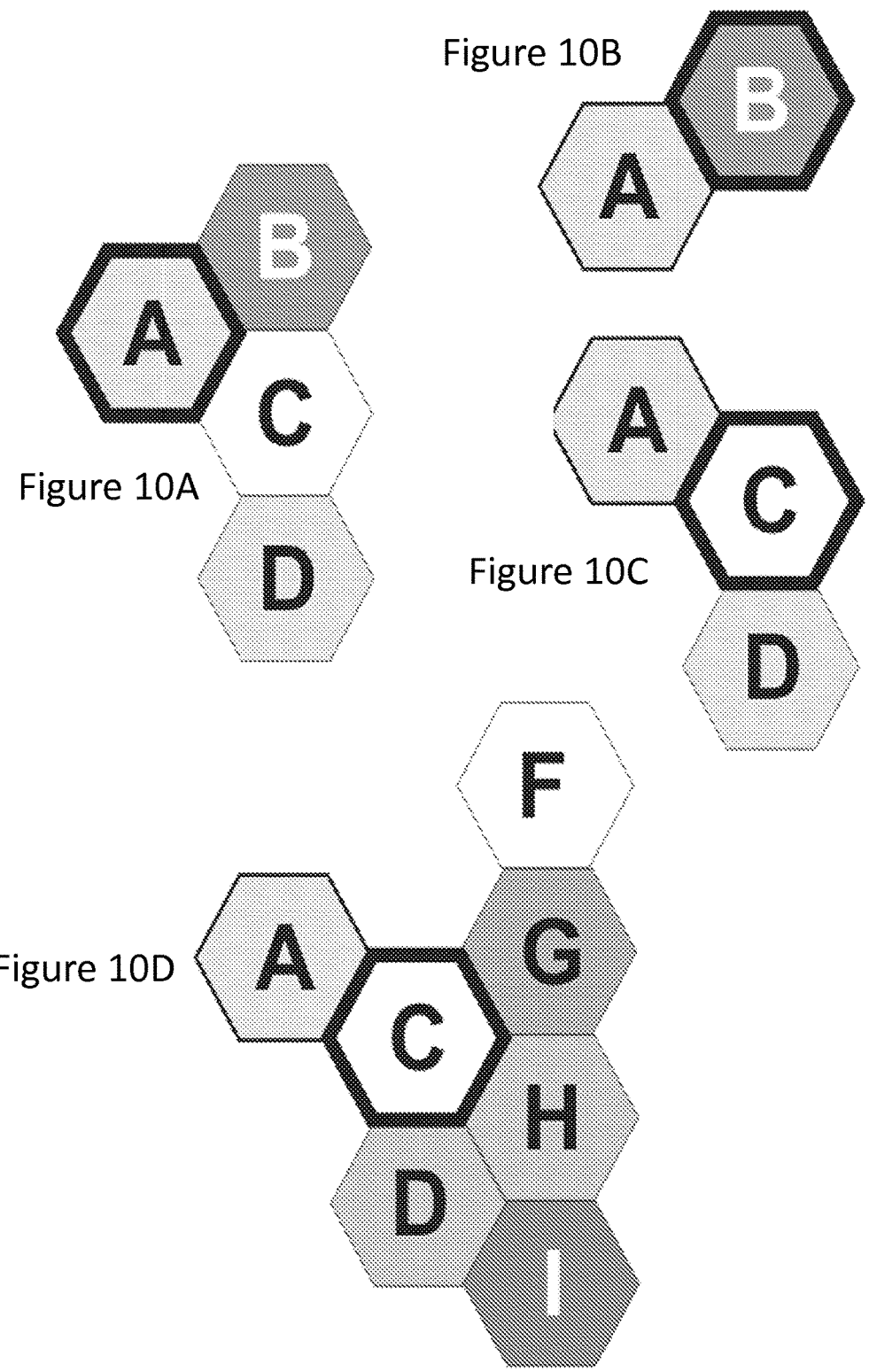

Figure 13
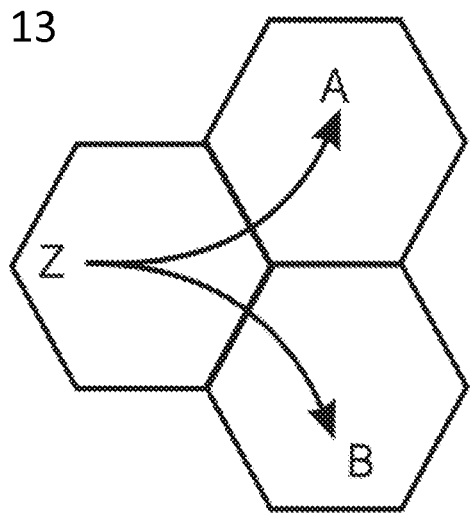
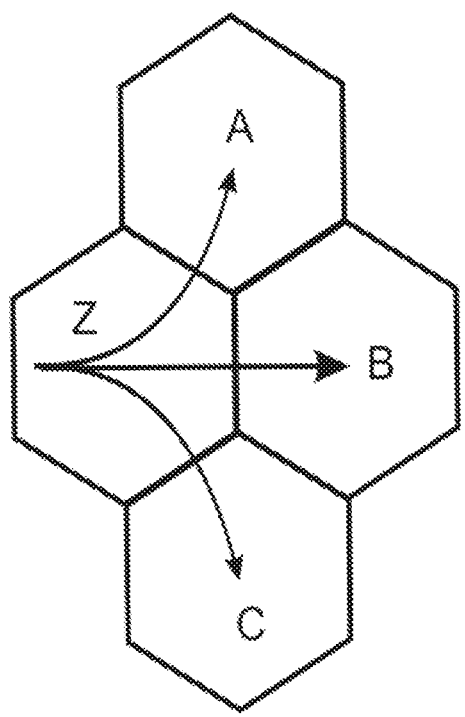
Figure 14

DECISION-ORIENTED HEXAGONAL ARRAY GRAPHIC USER INTERFACE

CROSS-REFERENCE TO RELATED APPLICATIONS

This application is a § 371 National Stage application of International Patent Application No. PCT/US2013/63777, filed Oct. 8, 2013 and entitled "DECISION-ORIENTED HEXAGONAL ARRAY GRAPHIC USER INTERFACE", which claims priority to and the benefit of U.S. Provisional Patent Application No. 61/711,895, entitled "HEX GUI" and filed Oct. 10, 2012, the contents of both of which are herein incorporated by reference in their entirety.

FIELD OF THE INVENTION

The present invention relates to graphical user interface, and more specifically to a decision-oriented graphical user interface utilizing hexagonal tiles.

BACKGROUND

Graphic User Interfaces have been defined typically as rectangular arrays of individually selectable icons, but there are a few with hexagonal icons, that can be packed tightly on a screen as in a beehive. Hexagons can also be found as isolated icons, organized into arrays where sides align. There are similar to strategy board games, like Chinese checkers, that have existed for millennia, the array of hexagons, or elements on a hexagonal field are used to define pathways to a goal for contestants to follow.

Smartphones and tablets have traditionally been used for connectivity and digital storage. With the advent of tracking cookies and other tracking technologies, it is not common for such devices to collect and integrate information and now assists in making decisions. Indeed, in the case routing of a trip using a map application of a global positioning system (GPS) device, a sequence of automated decisions is made in such devices to suggest a preferred path. This is the beginning of a trend to where the personal intelligent devices becomes an indispensable partner and advisor in most human decisions, the configuration of the graphic user interface of such personal intelligent devices will have a significant impact.

SUMMARY

The various embodiments are directed to a hexagonal graphic user interface (GUI) utilizes geometric properties of hexagons to interactively present a highly compact decision oriented interface suitable for presentation and control on personal information devices such as smart telephones, tablets, and wearable devices.

In a first embodiment of the invention, there is provided a method. The method includes the step of rendering a user interface including one or more primary icons, each of the one or more primary icons being a hexagon and representing an initial state. The method also includes the step of, responsive to the selection of a first icon from the primary icons, displaying one or more secondary icons, each of the secondary icons being a hexagon and positioned in the user interface in a hexagonal tiling (hextille) arrangement with respect to at least one of the first icon or another one of the secondary icons, each of the secondary icons representing additional states subsequent to the initial state along valid paths from the initial state.

The method can include, responsive to the selection of a second icon from the secondary icons, removing any of the secondary icons not associated with valid paths associated with a one of the additional states associated with the second icon and displaying one or more tertiary icons, each of the tertiary icons being a hexagon and positioned in the user interface in a hextille arrangement with respect to at least one of the first icon, the second icon, or another one of the tertiary icons, each of the tertiary icons representing further states subsequent to the additional state of the second icon along valid paths from the initial state and through the additional state of the second icon.

The method can also include, responsive to the selection of an edge of a second icon from the secondary icons, temporarily displaying one or more tertiary icons, each of the tertiary icons being a hexagon and positioned in the user interface in a hextille arrangement with respect to at least one of the first icon, the second icon, or another one of the tertiary icons, each of the tertiary icons representing further states subsequent to the additional state of the second icon along valid paths from the initial state and through the additional state of the second icon. Further, responsive to the sliding of the edge towards a one of the tertiary icons, the method can also include removing any of the secondary icons not associated with valid paths associated with a one of the additional states associated with the second icon and permanently displaying the one or more tertiary icons.

The method can further include, responsive to a tapping of the first icon, causing an altering of at least one of the secondary icons. The method can also include, responsive to a tapping of the first icon, causing an altering of the first icon. The method can additionally include, responsive to a tapping of an edge or vertex between adjacent icons, causing an altering of at least one of the adjacent icons.

In a second embodiment, there is provided a computer-readable medium having stored thereon a plurality of instructions for causing a processor to perform a method. The method includes the step of rendering a user interface including one or more primary icons, each of the one or more primary icons being a hexagon and representing an initial state. The method also includes the step of, responsive to the selection of a first icon from the primary icons, displaying one or more secondary icons, each of the secondary icons being a hexagon and positioned in the user interface in a hexagonal tiling (hextille) arrangement with respect to at least one of the first icon or another one of the secondary icons, each of the secondary icons representing additional states subsequent to the initial state along valid paths from the initial state.

The method can include, responsive to the selection of a second icon from the secondary icons, removing any of the secondary icons not associated with valid paths associated with a one of the additional states associated with the second icon and displaying one or more tertiary icons, each of the tertiary icons being a hexagon and positioned in the user interface in a hextille arrangement with respect to at least one of the first icon, the second icon, or another one of the tertiary icons, each of the tertiary icons representing further states subsequent to the additional state of the second icon along valid paths from the initial state and through the additional state of the second icon.

The method can also include, responsive to the selection of an edge of a second icon from the secondary icons, temporarily displaying one or more tertiary icons, each of the tertiary icons being a hexagon and positioned in the user interface in a hextille arrangement with respect to at least one of the first icon, the second icon, or another one of the tertiary icons, each of the tertiary icons representing further states subsequent to the additional state of the second icon along valid paths from the initial state and through the additional state of the second icon. Further, responsive to the sliding of the edge towards a one of the tertiary icons, the method can also include removing any of the secondary icons not associated with valid paths associated with a one of the additional states associated with the second icon and permanently displaying the one or more tertiary icons.

The method can further include, responsive to a tapping of the first icon, causing an altering of at least one of the secondary icons. The method can also include, responsive to a tapping of the first icon, causing an altering of the first icon. The method can additionally include, responsive to a tapping of an edge or vertex between adjacent icons, causing an altering of at least one of the adjacent icons.

In a third embodiment of the invention, there is provided a system including a display, a processor communicatively coupled to the display, and a computer-readable medium, having stored thereon a computer program including a plurality of code sections, where the plurality of code sections configured for causing the processor to perform the steps of a method. The method includes the step of rendering a user interface on the display including one or more primary icons, each of the one or more primary icons being a hexagon and representing an initial state. The method also includes the step of, responsive to the selection of a first icon from the primary icons, displaying one or more secondary icons on the display, each of the secondary icons being a hexagon and positioned in the user interface in a hexagonal tiling (hextille) arrangement with respect to at least one of the first icon or another one of the secondary icons, each of the secondary icons representing additional states subsequent to the initial state along valid paths from the initial state.

The method can include, responsive to the selection of a second icon from the secondary icons, removing from the display any of the secondary icons not associated with valid paths associated with a one of the additional states associated with the second icon and displaying one or more tertiary icons, each of the tertiary icons being a hexagon and positioned in the user interface in a hextille arrangement with respect to at least one of the first icon, the second icon, or another one of the tertiary icons, each of the tertiary icons representing further states subsequent to the additional state of the second icon along valid paths from the initial state and through the additional state of the second icon.

The method can also include, responsive to the selection of an edge of a second icon from the secondary icons, temporarily displaying one or more tertiary icons on the display, each of the tertiary icons being a hexagon and positioned in the user interface in a hextille arrangement with respect to at least one of the first icon, the second icon, or another one of the tertiary icons, each of the tertiary icons representing further states subsequent to the additional state of the second icon along valid paths from the initial state and through the additional state of the second icon. Further, responsive to the sliding of the edge towards a one of the tertiary icons, the method can also include removing from the display any of the secondary icons not associated with valid paths associated with a one of the additional states associated with the second icon and permanently displaying the one or more tertiary icons.

The method can further include, responsive to a tapping of the first icon, causing an altering of at least one of the secondary icons on the display. The method can also include, responsive to a tapping of the first icon, causing an altering of the first icon on the display. The method can additionally include, responsive to a tapping of an edge or vertex between adjacent icons, causing an altering of at least one of the adjacent icons on the display.

In the various embodiments, the hexagonal GUI can be utilized to direct users during a directed decision-making process. In particular, the hexagonal icons in the hexagonal GUI can be added, removed, or altered to assist and guide the user during the decision-making process. Thus, the hexagonal GUI can present features to guide users to preferred desirable decisions and away from undesirable decisions.

BRIEF DESCRIPTION OF THE DRAWINGS

FIGS. 10A, 10B, 10C and 10D show how tiles are added and removed based on selection of an tile in accordance with various embodiments;

FIG. 13 shows a two-way "horizontal" decision in accordance with the various embodiments;

FIG. 14 shows a three-way vertical decision in accordance with the various embodiments;

DETAILED DESCRIPTION

Figure 1:
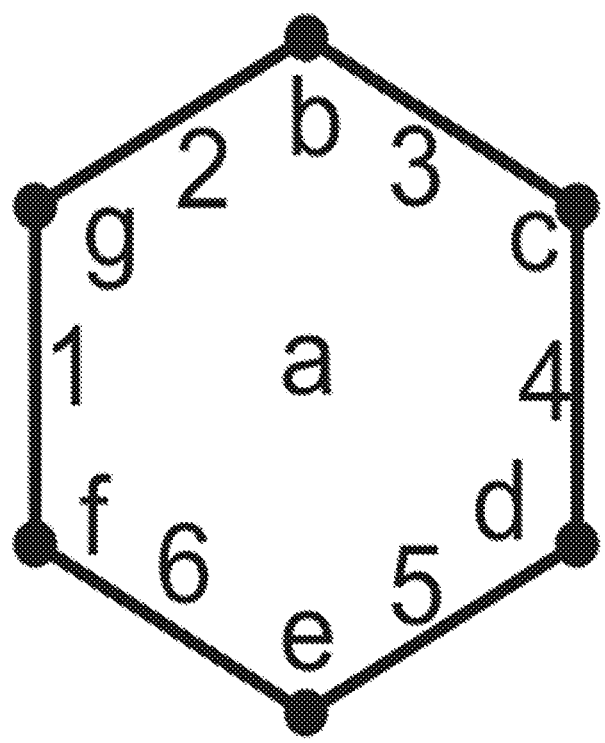
FIG. 1 shows selection points on a hexagonal tile in accordance with the various embodiments.

The present invention is described with reference to the attached figures, wherein like reference numerals are used throughout the figures to designate similar or equivalent elements. The figures are not drawn to scale and they are provided merely to illustrate the instant invention. Several aspects of the invention are described below with reference to example applications for illustration. It should be understood that numerous specific details, relationships, and methods are set forth to provide a full understanding of the invention. One having ordinary skill in the relevant art, however, will readily recognize that the invention can be practiced without one or more of the specific details or with other methods. In other instances, well-known structures or operations are not shown in detail to avoid obscuring the invention. The present invention is not limited by the illustrated ordering of acts or events, as some acts may occur in different orders and/or concurrently with other acts or events. Furthermore, not all illustrated acts or events are required to implement a methodology in accordance with the present invention.

The various embodiments are directed to a GUI designed to optimize singular and sequential decisions, such as those typical of Episodal Social Networks (ESNs) that work interactively with the user. ESNs are described in more detail in International Patent Application No. PCT/US2012/052404, filed Aug. 25, 2012 and entitled "EPISODIC SOCIAL NETWORKS", the contents of which are hereby incorporated by reference in their entirety. The Nature of ESNs is that they are defined by sequentially interdependent decisions. A graphic User Interface that can define and display such decisions is therefore optimized for ESN Development, User Operation and Display. It becomes especially useful in high stakes environments (e.g., coordinated teams in healthcare).

In the various embodiments, hexagon are utilzied for the GUI because of the properties of hexagonal tiles. That is, if a user can interact with the hexagonal GUI when a tile, such as that shown in FIG. 1, at the center (a), inside of an edge (1-6), or on an inside corner (b-g), i.e., at a number of activation points. The potential number of activation points is the number of sides+the number of inside corners+the center) The net result is that a single hexagon can be activated in many (13) ways, unlike other types of shapes that can be closely packed, such as rectangles and triangles. That is, neither triangles (7-ways) nor squares (9-ways) have so many potential selections in a single figure.

Figure 2:
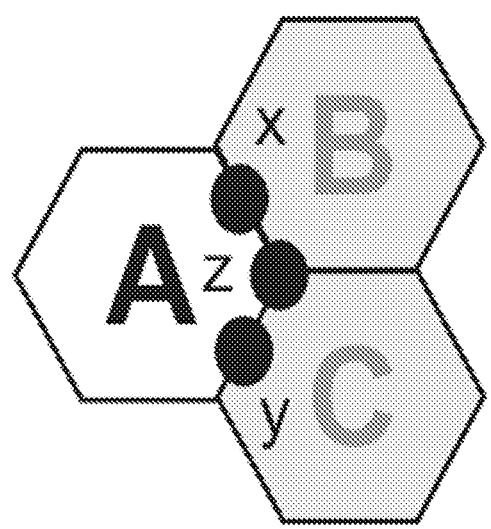
FIG. 2 shows selection points between hexagonal tiles in accordance with the various embodiments.

Another advantage of the hexagonal GUI of the various embodiments is that by detecting simultaneous activation of adjoining figures, such as at a junction of two edges (x or y) or the intersection point (z) of 3 adjacent tiles, as shown in FIG. 2, the multiple activations can define a unique collection of activated inputs that can be used to define and activate unique functions. This can be advantageous, especially when dealing with handheld, mobile devices, such as smartphones or other personal information devices. That is, since screens of personal information devices are generally limited in size, it is desirable to create as many selections and detectable decisions as possible in as small a space as possible to provide a large functionality in the limited space. Therefore, the various embodiments allow the GUI to utilize even within boundary lines of one tile or figure as input.

In the case of a touch screen on a personal information device, it is generally easiest to detect the crossing of the boundary as opposed to crossing a corner or point of intersection. It is merely a case of resolution of the touch screen. The boundary line size is really determined by the touch space of a finger or stylus (pointing device)—so comparison of the space efficiency of eligible figures (triangles, rectangles and hexagons) requires that they have the same edge lengths and comparable internal area for maneuvering the pointing device, i.e., are of the same scale Therefore, since it is preferred to detect the crossing of a boundary and it is desirable to pack the tiles tightly, one way to meet both objectives is to pack the figures with no interstitial space. FIGS. 3A-3D and 4A-4B show that only three types two-dimensional shapes can be packed in a plane without interstitial space. Those shapes are: three-sided shapes (such as triangles shown in FIGS. 3A-3B), 4-sided shapes (such as squares or rectangles shown in FIGS. 3C-3D), and 6-sided shapes, such as hexagons.

Figure 4A:
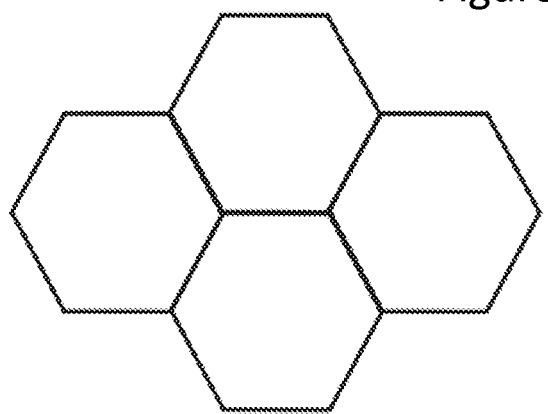
FIGS. 4A and 4B show examples of packed hexagons.
Figure 4B:
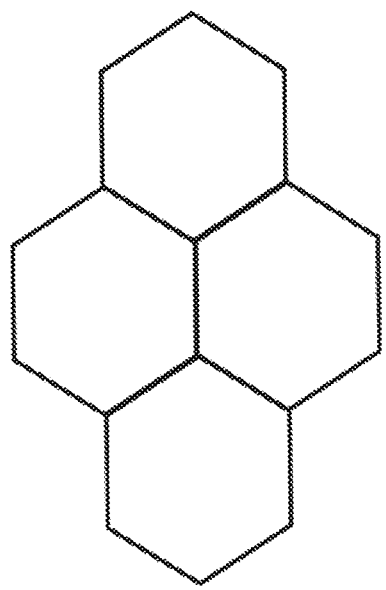

Hexagons cannot be ordered in a skewed fashion, like squares and triangles, but they have basically the two orientations shown relative to a rectilinearly shaped display (one where two of the edges are vertical and the other where those edges are horizontal, as illustrated in FIGS. 4A and 4B, respectively). Other figures can be packed without interstitial space, but the result is not a two-dimensional figure suitable for simple graphical presentation a two-dimensional display.

For example, pentagons and mixes of shapes can define three-dimensional figures that can be displayed with three-dimensional graphics on a two-dimensional display. For example, a three-dimensional sphere can be generated using pentagonal tiles and could be rotated to show all of its pentagonal tile faces. However, such presentation misses the objective of a simple, two-dimensional GUI where the information of multiple tiles can be presented simultaneously.

Figure 5:
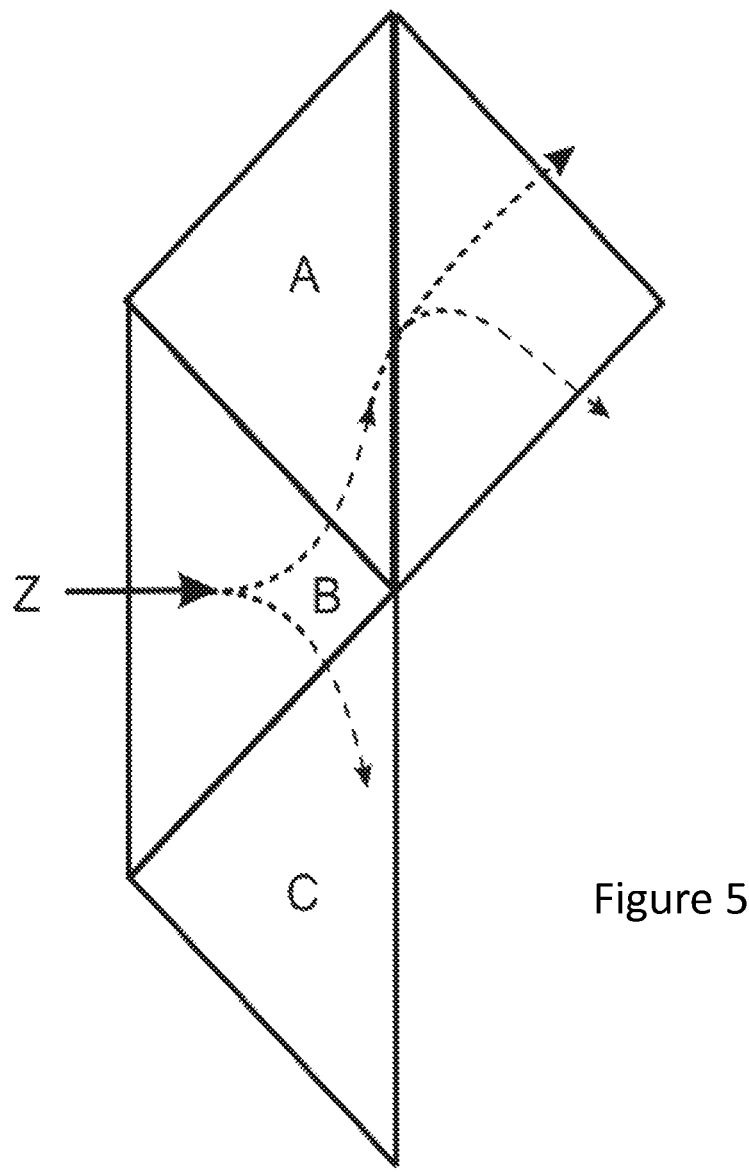
FIG. 5 shows how a triangle provides a two-way choice.
Figure 6:
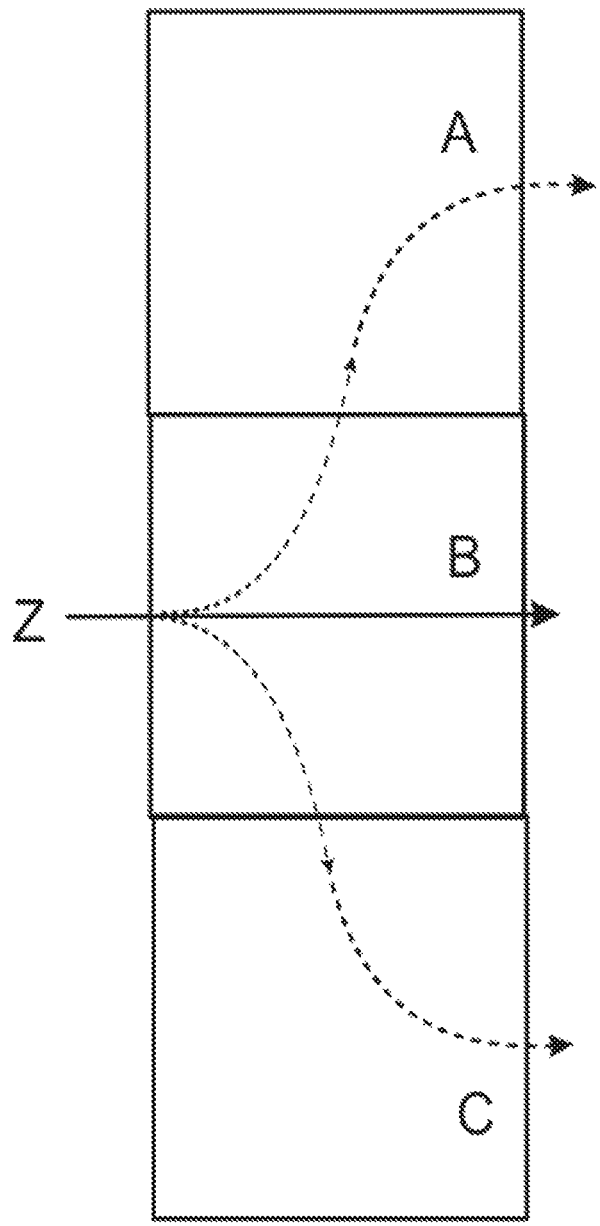
FIG. 6 shows the two-way or three-way choice with rectangles.
Figure 7:
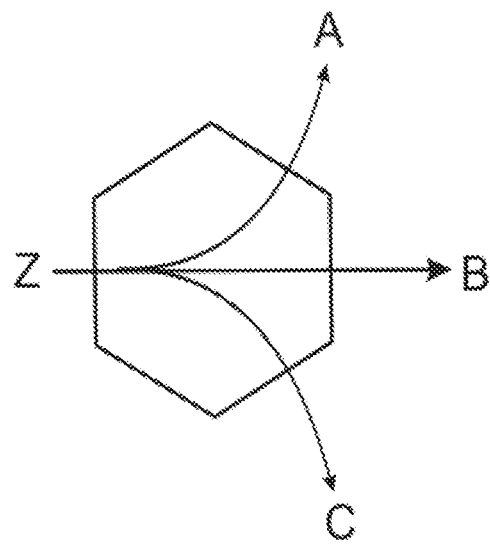
FIG. 7 shows a 3 way decision with a hexagon according to the various embodiments.
Figure 8:
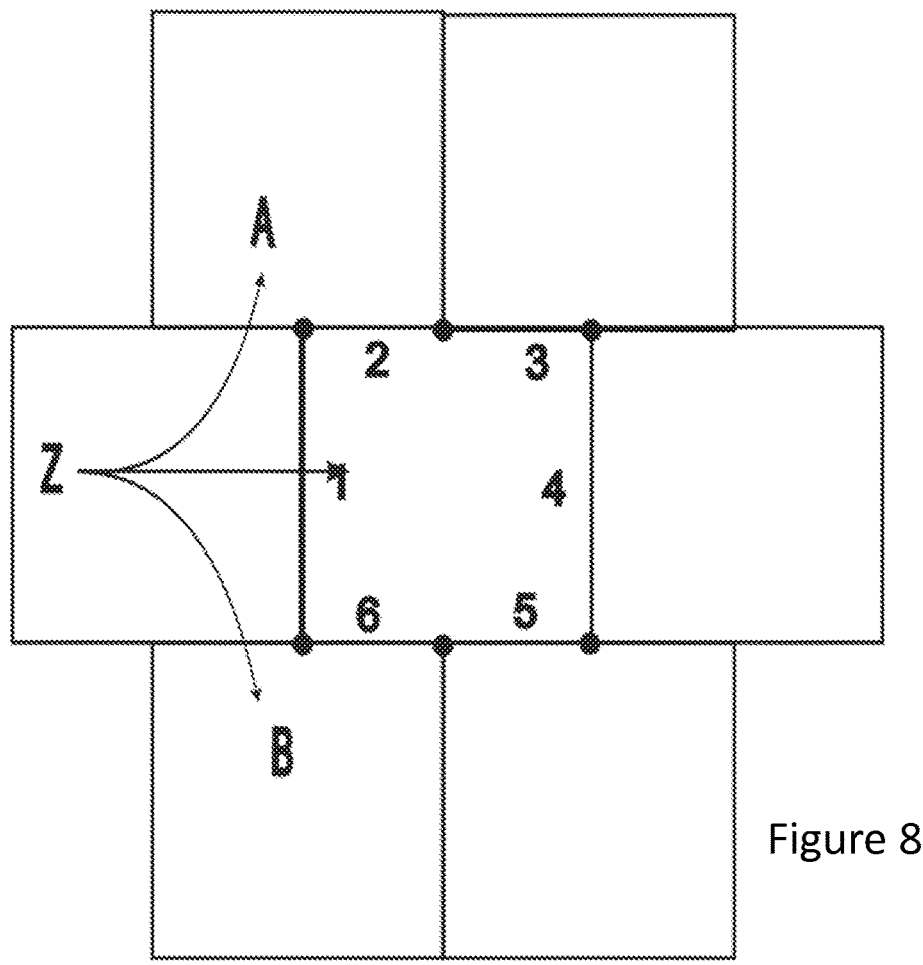
FIG. 8 shows a three-way decision with skewed squares (rectangles)

To illustrate the advantages of a two-dimensional hexagonal GUI of the various embodiments, the discussion now turns to FIGS. 5-8. FIG. 5 shows a triangular array with a two-way decision path exiting the boundaries to the right of triangle B. It actually requires two more triangles (A, C) in order to allow the decision path to continue from left to right. Similarly, squares of rectangles in an array in FIG. 6, require additional figures to allow the decision process to progress linearly (the equivalent of six triangles). In contrast, a hexagon, as shown in FIG. 7, requires no additional figures. As a result, even though a hexagon might be larger in size than the triangles on a screen, it uses area on a screen more efficiently.

Figure 3A:
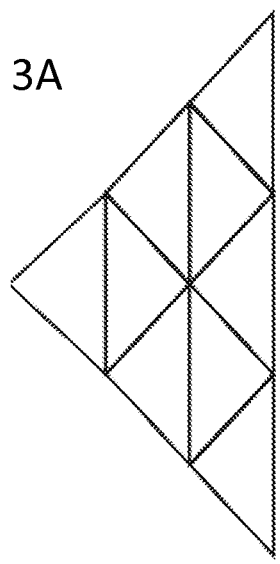
FIGS. 3A, 3B, 3C and 3D show examples of packed triangles and squares.
Figure 3B:
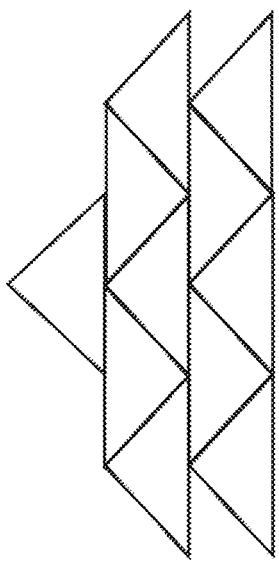
Figure 3C:
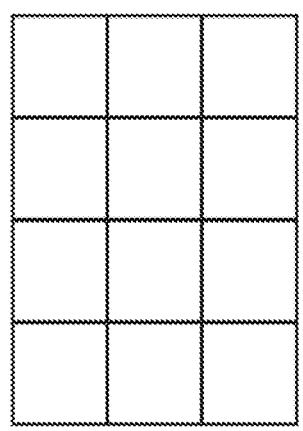
Figure 3D:
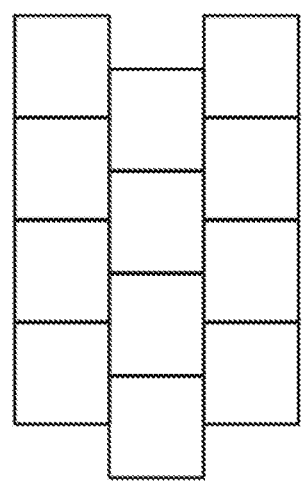

Conceivably, a skewed arrangement of shapes, as previously illustrated in FIGS. 3B and 3D might permit multi-way decision depiction in as small a space. However, as can be seen from FIG. 8, that such a pattern is actually a special case of the hexagon. Indeed, for the boundary length between tiles to be equivalent, the skewed squares must be equal on sides (1-6) and in practice it becomes problematic to determine if the boundary is crossed in the first half of the rectangles side, or the last half (e.g. side 2 versus side 3) Therefore, based on the above advantages, it is seen that (typically equilateral) hexagons are the optimal tile shape for a condensed, decision oriented display on a two-dimensional touch screen display.

Figure 9A:
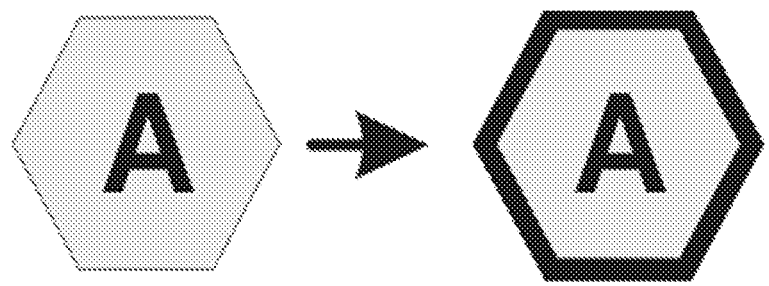
FIGS. 9A and 9B show an exemplary tile selection in accordance with the various embodiments.
Figure 9B:
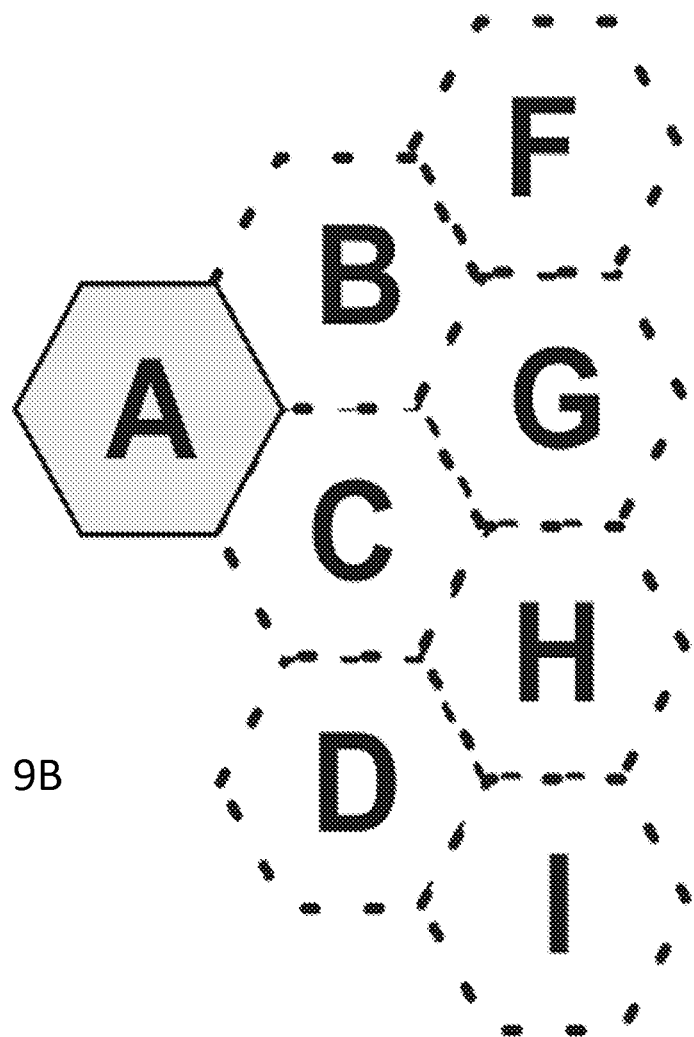

Now turning to FIGS. 9A-9B, 10A-10D, 11, and 12, an exemplary operation of a hexagonal GUI for decision making, in accordance with the various embodiments is illustrated. First consider a simple selection. That is, tile A is presented as shown in FIG. 9A. At this point, there are several potential options (B through I) that are hidden from the user, as shown in FIG. 9B. When tile A is selected, it is highlighted by making the border bold (as shown in FIG. 9A) and consequently options B, C and D become visible to the user, as shown in FIG. 10A.

In addition to showing options at step 10A, the tiles can include some other type of indicia to distinguish or highlight tiles. This indicia can be used to indicate desirable or undesirable goals, difficult options, or any other type of information regarding a particular option. The indicia can include, but is not limited to, colors, markings, symbols, shading, or other features can be used.

Further, the various embodiments are not limited solely to visual features. For example, the hexagonal GUI of the various embodiments can also be used with a tactile response screen. Thus, roughness, or height or pressure can be used to substitute for darkness or shading of a tile. Moreover, the characters might be Braille dots or other tactile indicia. Such an interface can be used for the sight impaired to navigate through streets and walkways, or when it is desirable to not distract the user's vision or concentration on another display, as in a strategy or control interface for a vehicle pilot (fighter aircraft, drone, etc). Moreover, these tactile features can be used in combination with visual features. Similarly, other types of sensory or feedback features can be used to interface with the senses, including, but not limited to audio features, vibratory features, heat/cold features, or electrical stimulation features. Thus, in the various embodiments, a device with the hexagonal GUI would include suitable transducers, heating/cooling elements, or whatever other types of elements are required for providing the other sensory or feedback features.

These can be used to identify certain types of options, including options that are preferred by the user or an entity associated with the GUI. For example, as shown in FIG. 10A, option C is recommended by highlighting or lighter colors, option B is discouraged and presented as an un-recommended, potential "dead end", by being dimmed with the "B" character inverted to light for contrast.

In some cases, some future options may be presented, such as those preferred by the user or an entity associated with the GUI. For example, as shown in FIG. 10A, option D can be shown but is not yet available as an immediate choice as it would require selection of tile C. Thus, is option D is preferred for the user, the GUI indicates how the user may reach this option.

Selection of the un-recommended tile B, would remove choices C and D, as shown in FIG. 10B. In some embodiments, the selection can also be accompanied by an alert for the user, possibly with a warning (e.g. audible, vibration, visual screen flash). At this point, the only option the user would have is a return to the configuration of FIG. 10A by selection of tile A again. Selection of C, as shown in FIG. 10C initially removes option B and can cause further highlighting of option D or other options. Additionally, the GUI can display new options, such as F, G, H, and I, as shown in FIG. 10D.

In the configuration of FIG. 10D, tile F is suggested as an eventual goal, similar to D in FIG. 10A, but only after G. is selected. In FIG. 10D, tile G is presented as a darkened tile which may have some negative impact, such as risk or difficulty. Note that in contrast to the negative impact for tile B, the "G" character in tile G is not inverted, indicating that it is not a dead end. However, tile I is presented inverted as a dead end, similar to choosing tile B. In this example, each decision to move through the GUI has recommendations, warnings, consequences and results following a flow chart provided in FIGS. 11 and 12. Note: the terms "tile" and "Cell" are used interchangeably to refer to specific hexagons in the process.

Figure 11:
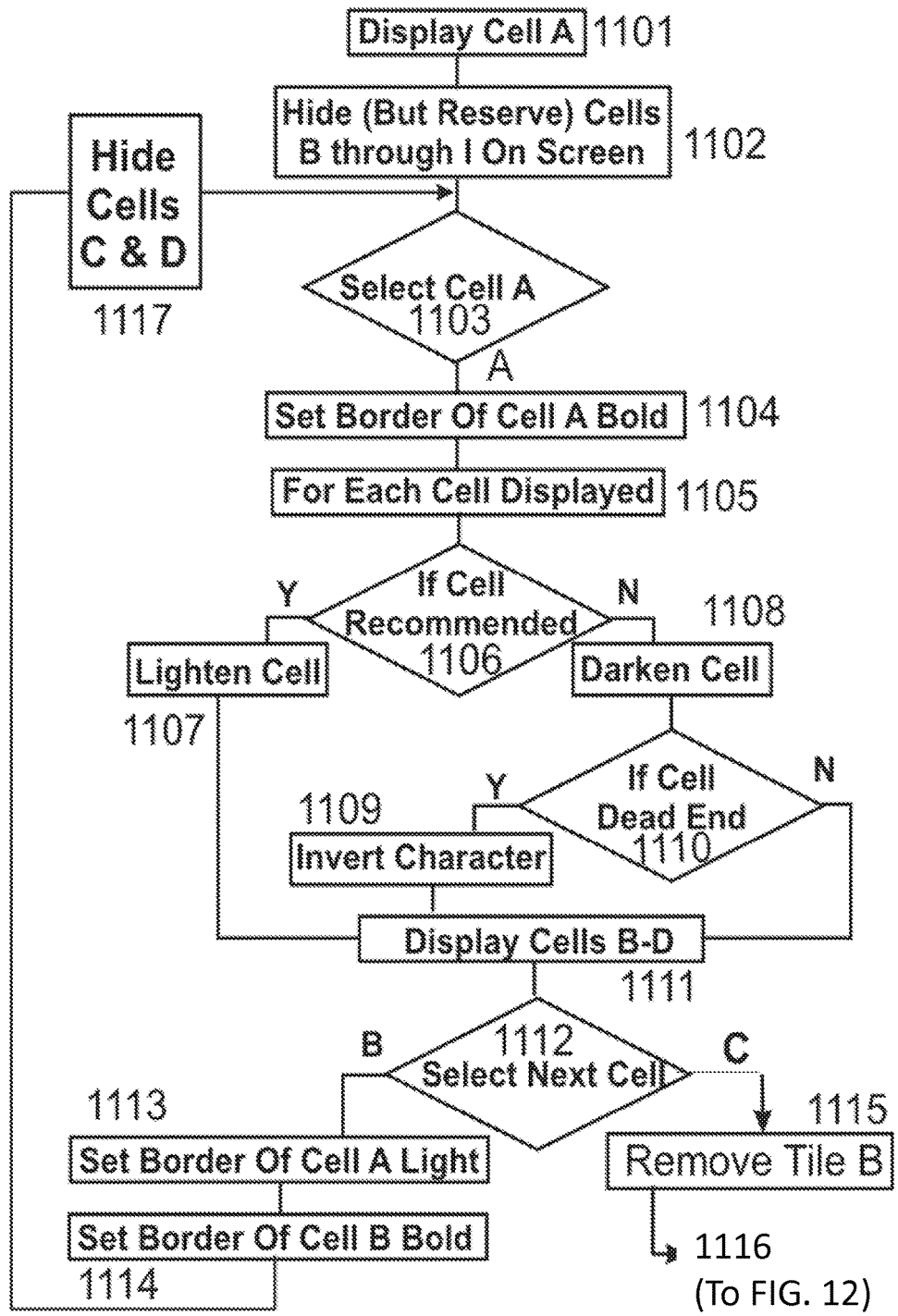
FIGS. 11 and 12 show flowcharts of exemplary tile selection processes in accordance with the various embodiments.

The process flow behind the GUI begins in FIG. 11 with step 1101 as the hexagonal tile or cell A is first displayed as in FIG. 9 top with a dark "key Character" inside—in the example the key character is a capital A. Space is reserved in the display for all the additional tiles B through I in FIG. 9B in step 1102 of FIG. 11. Step 1103 is the detection of the selection of cell A on the touch screen and the display of the emphasized response (as in FIG. 9A) is performed at step 1104 of FIG. 11. An iterative routine then begins with step 1105 where each cell to be eventually displayed is shaded or colored to represent if it is recommended, at step 1106, by lightening the inside, at step 1107, or darkening the non-recommended cells, at step 1108. If a cell is dead end, at step 1110, the tile is darkened further and the key character inside the cell is inverted at step 1109 to a light color. At this point (corresponding to FIG. 10A), the tiles B-D are displayed at step 1111, while the tiles F, G, H, and I are not yet shown.

The decision process is then started and in step 1112 the next tile is selected. If the dead end tile B is chosen, as in FIG. 10B, the highlight moves to tile B at steps 1113 and 1114 and cells C and D are hidden in step 1117. As A is the only possible choice, control is passed to tile A, at step 1103, where the process repeats upon selection of tile A. Had tile C been chosen at step 1112, tile B would no longer be displayed (step 1115), as shown in FIG. 10C.

Figure 12:
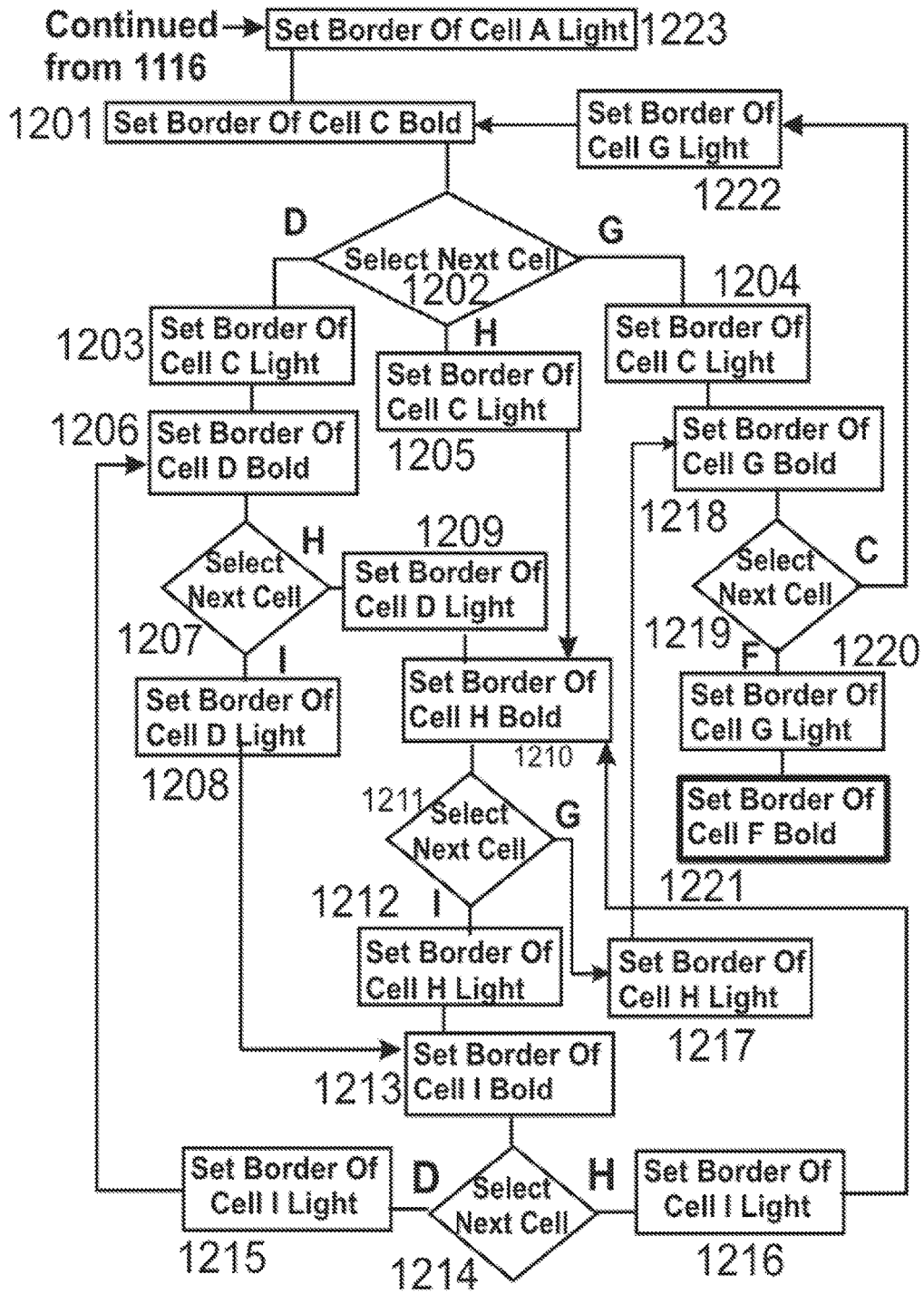

Now referring to FIG. 12, starting from step 1116 in FIG. 11, control would pass through to step 1223 to set the border of cell A light and "C" is highlighted at step 1201. A three way choice is available (at step 1202) for selecting between Tiles D, G, or H. If D is chosen the highlight moves from C to D at steps 1203 and 1206. Had H been chosen at step 1202, the highlight would have moved from C to H at steps 1205 and 1210. Similarly, at steps 1204 and 1218 the highlight the highlight is moved to tile G if it had been chosen at step 1202.

At step 1207, Tile D has the option of moving to either tile H or the dead end tile I. If tile I were chosen, it is highlighted through steps 1208 and 1213 and the user may return back to tile D through 1214 with the highlight returning to D through steps 1215 and 1206. Tile D could also move to tile H through 1207 with the highlight moving to H at steps 1209 and 1210. It is possible for H to move to Tile I at step 1210 with the highlight moving in steps 1212 and 1213. The highlight could then return to H at step 1214 with the highlight moving at steps 1216 and 1210.
Tile H could also move to Tile G at "1211" with the highlight moving through "1217" and "1218".

Tile G was also the third choice at step 1202 from Tile C, with the highlight moves from C to G at steps 1204 and 1218. Either way that the user would arrive at Tile G, as it is the only path to Tile F through step 1219 with the highlight moving in steps 1220 and 1221". The User could also return to Tile C from Tile G at 1219 with the highlight moving in 1222 and 1201. Basically, FIG. 12 shows the logical operations after FIG. 10D.

Note that the successful decision path can remain displayed and by design may be the outline of a recognizable character, where alternately a path representing a learned character may be used to repeat a decision path. Further note the complexity of all this logic is compactly represented interactively in just 8 tiles of the HEX GUI. In this fashion, the user can be guided through decisions and ESN choices through the GUI. Variations on this concept may have optional tiles appear if a selected tile is nudged in the direction of an option by moving the finger or stylus near the edge or interior angle between two choices. In effect this is giving a hint of the outcome. A hint is stimulated by holding contact with the boundary or boundaries with an inside corner, as if to move it into a new tile to make a selection, without lifting contact.

Another way of testing decisions and potential outcome a step ahead would be "smudging". Smudging allows the user to trace their finger or stylus over a surface into another tile without releasing contact. Releasing contact may be defined as ending the string or accepting a decision. A string may define a word, series of selections, or sequence of ESNs. One objective is to define an intuitive coding method for ESNs using this methodology for input, testing and display.

Not all options may be displayed until "tested" by pressing and holding on a boundary, some may be hidden and others viewable. These hidden options, may be mutually exclusive with other testable options—and may be temporary with time, selection history, or other conditions. Again options may change with time or history or other conditions. Testing is a way to preview an option, without selecting it. The option may be ephemeral, not available to all users, dependent on prior selections, or placed to encourage user to take an option that may disappear.

Indeed, an option may also select a cascade or, define a sequence of options or actions that occur spontaneously as a consequence: Such as a choice of a major in an academic environment, or a sequence of treatments once a given disease is diagnosed by this method. These options may be lifestyle options in a healthcare situation, courses in an academic setting, or even alternatives in a computer dating and matching environment. This GUI can also be used to simulate a complex series of decisions and display multiple alternative paths to an outcome. To illustrate these concepts, one can consider an ESN example using FIGS. 10A-10D in which a patient enters an emergency room in step:

A=Initial determination is heart attack in progress
B=transport to another facility; this is an invalid choice and mutually exclusive with C
C=stabilize and diagnose treat locally (the recommended decision)
D=Do nothing or Declare DOA (Unlike the flowchart, there is no return path to C) From C there is a decision path through G: the Patient has advanced Coronary Artery Disease
G=is a Catheterization (a slightly risky procedure), the degree of blockage can be determined
G=is a prerequisite to F
H=A stent could be installed, if blockage is slight; however
I=The prognosis I is poor with extensive blockage, or muscle damage, and patients may die D
F=is a coronary bypass operation, optimal if only obstruction no muscle damage (2% failure) Coronary Bypass Surgery F is preferred option on patient this age with no permanent damage to heart.

While there is no substitute for human judgment and diagnosis, such a decision tool could be useful for the reservation of operating rooms, equipment (heart-lung machine), specific skills (cardiac surgeon), recovery and hospital space, materials, blood and the like. It is merely an example. There could be multiple ESN's involved—each with a prescribed multi-stage approach. This amounts to a multi-user care plan accessible by handheld and mobile devices from any point on the globe per FIG. 19. It is team oriented.

Acquisition and transport to care center
Stabilization
Diagnosis
Patient advisory
Preparation
Surgery
Recovery
Convalescence
Cardiac Rehabilitation.

Figure 19:
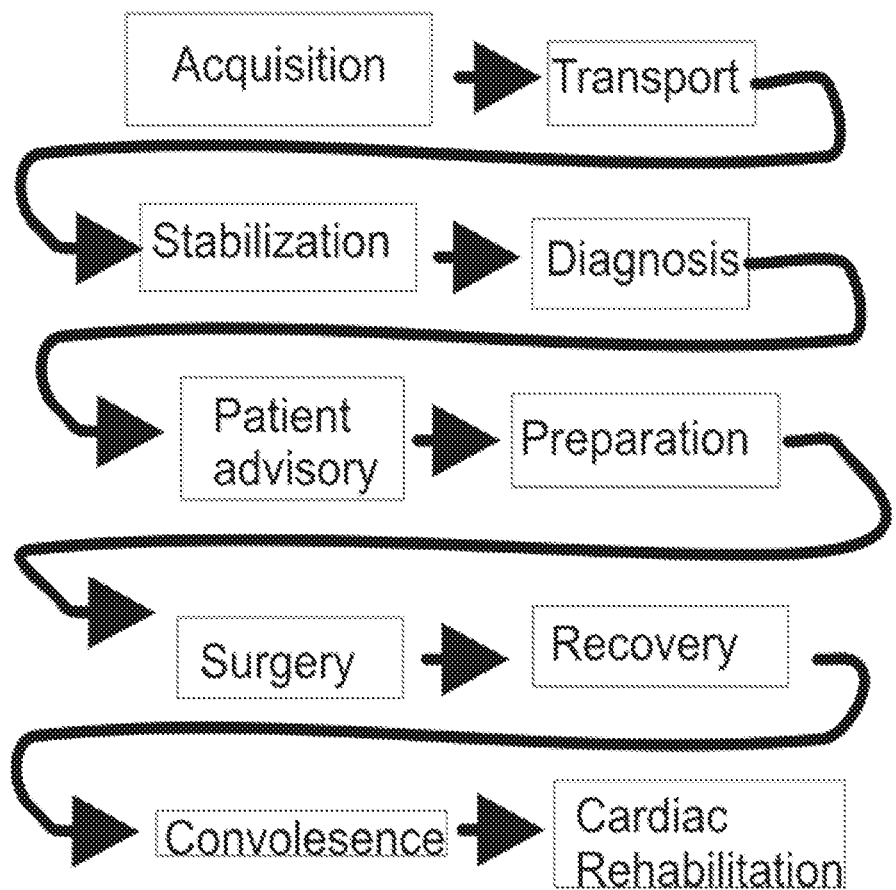
FIG. 19 shows an exemplary sequence of episodic social network that can be managed using a GUI in accordance with the various embodiments.

Further multiple sequential ESNs, all managed from a hexagonal GUI as in FIG. 19, can integrate the ability of the mobile system to confer with the cloud database, allowing continuous interaction between healthcare participants. The patient moves conditional from one stage of treatment, care, transport, specialized Care providers, and therapies. Patients and services can at all stages be managed and interact with the cloud—database system using compact hand held and tablet systems easily held on the person of all participants in a care facility, hospital or treatment program. Each tile of the system can be broken down in to sub elements and managed via service chain management practices. Further, stages in the sequence can integrate data automatically collected— such that the user his halted in the decision sequence to be alerted.

The hexagonal GUI of the various embodiments can be part of an integrated system of connectivity that links a common Internet database in the cloud with hospitals, medical education, providers and patients as well as emergency services using an array of commonly available digital connection devices. The power of this graphic user interface is its ability to display and acquire a large amount of information from human held devices, automated data systems, instruments and all phases of healthcare—and do it in a compact and easy to use, format feasible with small screen devices. The decision intelligence may be local to the handheld device or distributed over multiple connected machines, as in a cloud. In fact, in some embodiments, users of portable devices may actually be unaware if the data and background logic is local or remote. The location of data and logic may interactively change between local and remote depending on the complexity of a decision and the amount of data required to support the decision. Further, in a distributed embodiment, devices may confer with each other as required for the user.

Another potential utility of the various embodiments is in providing decision arrays. As previously noted, there are 2 orientations defined for hexagonal tile orientations. One is called "Vertical" and the other is called "Horizontal" based on their alignment relative to a rectilinearly shaped display: Horizontal (as shown in FIG. 13) where 2 edges of each hexagon are horizontal) and Vertical (as shown FIG. 14) where 2 of the edges are vertical. As can be seen from the figures, vertical tiles can define a three-way decision and horizontal tiles can define a two-way decision.

Figure 15:
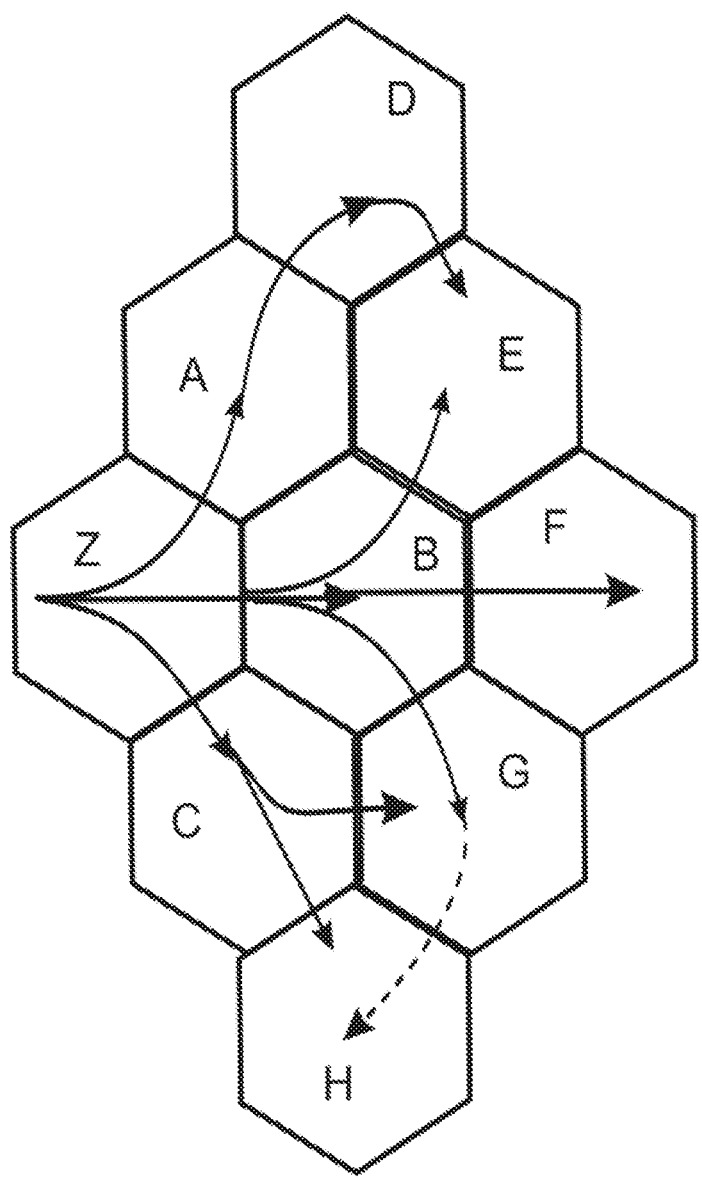
FIG. 15 shows an exemplary decision tree made of three-way vertical decision hexagons in accordance with the various embodiments.
Figure 16:
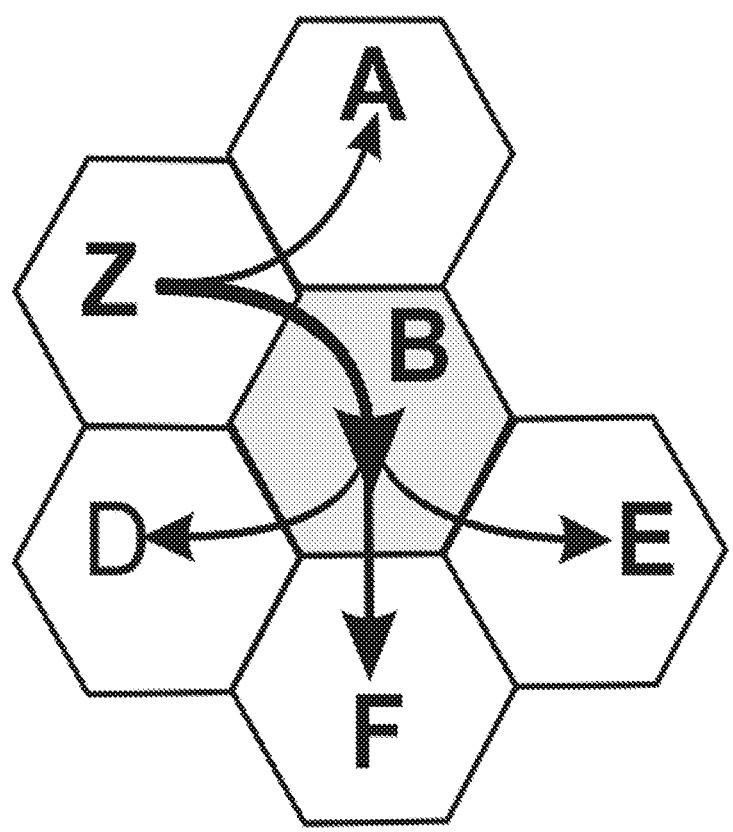
FIG. 16 shows an exemplary decision tree combining vertical and horizontal decisions in accordance with the various embodiments.

FIG. 15 shows how a complex decision array can be formed from combining vertical tiles and similarly a "top down" array can be defined using horizontal tiles. FIG. 16 shows that vertical and horizontal orientations can be combined into arrays, in this case beginning at point z. This is effectively the logical statement Z=A or [[D or E or F] given B]: a two-way decision followed by a three-way decision.

Figure 17:
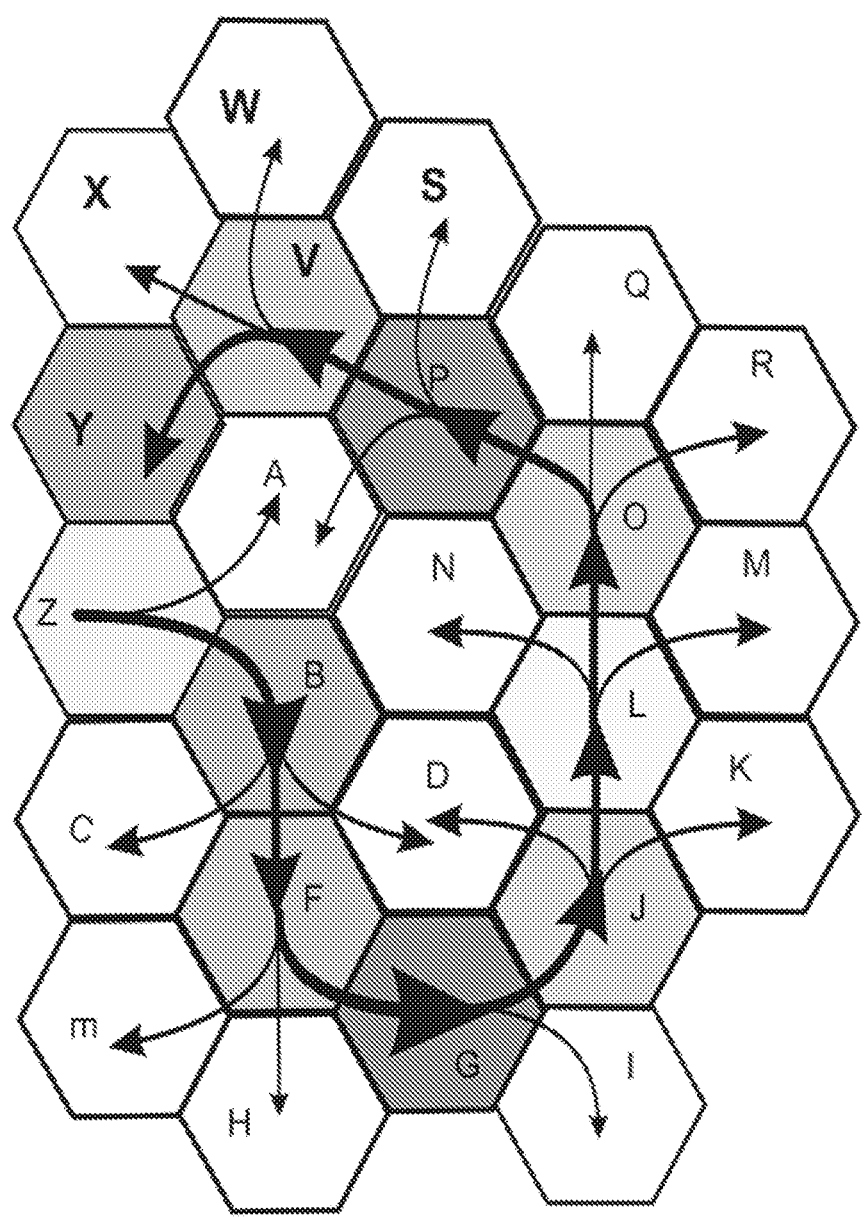
FIG. 17 shows an exemplary decision tree with looping in accordance with the various embodiments.

Without trying to define the logic statement, it can be seen that FIG. 17 shows an example of a very complex sequence of decisions with looping and iterative options beginning at point z as well. These complex arrays can be used to define a series of recommended decisions, as an expert system. For example, the expert system may be for the standardized diagnosis of a disease and subsequent/alternate modes and methods of treatment.

Figure 18:
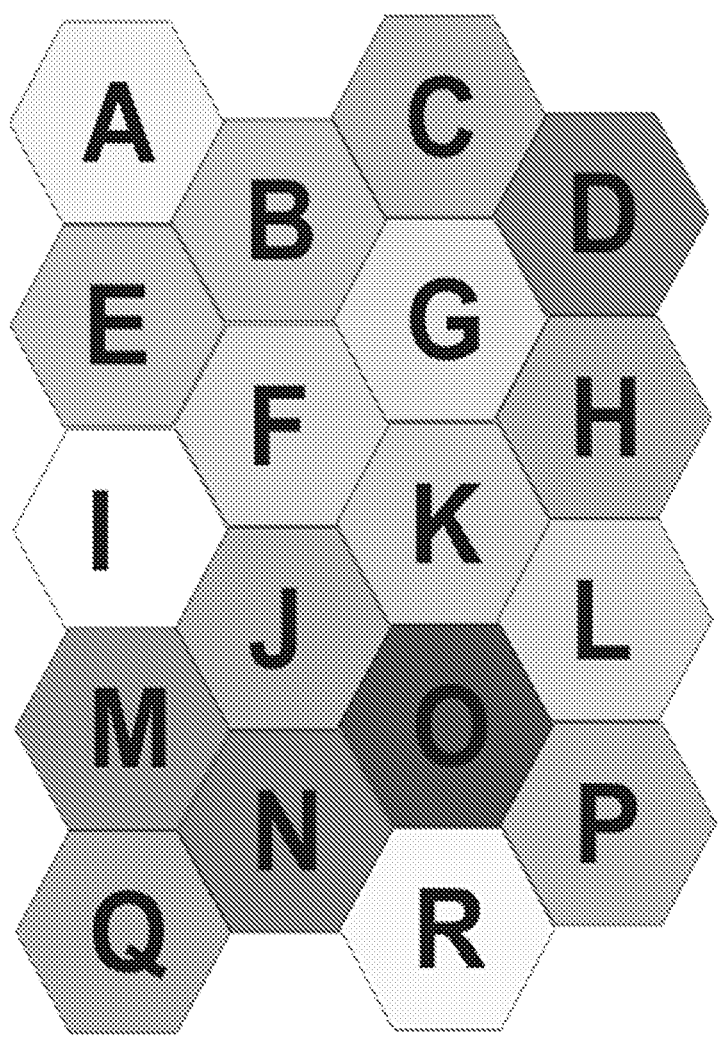
FIG. 18 shows an exemplary "hive" or array of hexagon tiles in accordance with the various embodiments.

A collection of organized tiles, such as those in FIG. 18, can be called a "hive, showing that a very complex decision array such as that of FIG. 17 can be presented in an interactive way on a small two-dimensional display, typical of a personal intelligent device, smart phone, tablet, netbook, wearable or the like.

There could be a avatar like agent at the terminal end that represents the ESN process and the hexagonal GUI of the various embodiments could be used to represent that process. Over the long term, this personal intelligence could be something that matures with the user, perhaps introduced in childhood. For example, in the case of simulation games potentially and there may be some means to envision all the potential outcomes depicted as animation or storyboard.

For example a child could learn the rules of football in a simulation, and with experience create an advanced understanding of strategy and depict the strategy of a play to see its outcome through the hexagonal GUI of the various embodiments.

One common motivational technique is to have an individual imagine what it would be like to achieve a certain goal. A decision oriented system could work back from that goal to show the steps and alternatives to achieve the goal, as well as the benefits, responsibilities and unforeseen sacrifices and limitations that may occur once the goal is attained. Say a $6^{th}$ grade child wished to become a doctor—he could be shown the logical steps to get there (premed in college or engineering with premed electives) with all the steps to get these prerequisites and sacrifices (presented as decisions). Each of the stages could be followed as ESNs presented through a story-board, or even motion visuals and depicted on the decision interface. Bad decisions, alternatives, shortcuts could be shown. Once the goal is achieved, as in the case of the physician, there may be extreme demands on his time, stress, emotional involvement that can also be shown as hurdles to a given professional lifestyle.) Indeed, we may be able to script and interactively exercise our own alternative career dreams during formative years in this fashion.

Because strategies, decisions, responsibilities can be compactly present and coded through a portable and personal information device using the hexagonal GUI of the various embodiments, it can be seen that this ability to compress the presentation and interaction with a decision process can be used by deployed teams aligned to a common purpose. For example, some portable information devices can be for inputting strategy at executive levels and devices at other levels may implement the smaller steps within that strategy, with a common system monitoring compliance and events.

Consider a group of firefighters coordinating a fire in a high-rise building. Command may have set down a general scripted and simulated strategy though a desktop system which may use a hexagonal GUI in accordance with the various embodiments for consistency with portable field devices to be used when implementing the strategy during an actual fire. A field commander may define, test, and delegate strategies to firemen within the building. Individual firemen, responding to those commands may even have tactile interface devices, such that they could navigate through smoke for example.

Each stage of the strategy might be a separate ESN. Similarly, law enforcement, battlefield, border security, customs, education, entertainment, hospitality, banking, credit, finance, manufacturing, process control, communication, etc—anywhere that teams of dispersed yet networked individuals coordinate complex decisions and activities could toward a common goal.

Other potential uses and features of the various embodiments that permit complex decisions to be displayed, proctored, or interacted with on a portable device include:
  A popover(s) or tool tip can be present when stimulated that explain each tile's function, status, options, etc, with suggestions.
  The hexagonal GUI can be pre-loaded, programmed, heuristically collected, or downloaded with "expert decision tree modules for specific activities with all (or most all) anticipated contingencies embedded. For example, decision processes may be packaged for specific complex decisions: how to buy a home or car, obtain a loan, get into college, navigate a career in a corporation politically, handle money, obtain the best medical care, bid in online auctions, handle a medical (or any) emergency, buy insurance, handle bankruptcy, arrest, foreclosure, select home maintenance services, take a given prescription, seek (and interview for) a job, tell when someone may be lying, and other decision scenarios that inexperienced individuals, might find challenging. Modules could be defined for many similar scenarios requiring mature judgment by inexperience individuals.
  The hexagonal GUI can be used to record how an individual handles such scenarios—for eventual evaluation/improvement/learning/recovery. This may include centralized data collection for a heuristic system that learns from many-for many.
  The hexagonal GUI can be used to program decision trees, e.g., such as above
  The hexagonal GUI can be used to navigate to a destination or goal in the face of multiple alternatives such as traffic, breakdown, theft, illness, multiple carriers and transport services, luggage, travel bargains-upgrades, etc.
  The hexagonal GUI can be configured to do programmed tasks, cook a meal, mix drinks, maintain a specific make and brand of car, operate a smart phone, etc.
  The hexagonal GUI can be configured to learn academic or performance experience.
  To guide users to vote intelligently, or with an agenda or party line.
  To help user rehearse and understand etiquette with social response and graces. E.g., which fork to use, do I send a thank you note, how to ask for and know how to act on a date.
  To help users learn how to understand people, one's own emotions, anticipate reaction, win friends and influence people—step by step guidance—including situational avoidance.
  The hexagonal GUI can be used by specific professions to perform specific tasks:
  e.g. law enforcement might be guided in how to interrogate, legally handle an arrest, what specific charge best fits an offense. Or a lawyer might use a similar decision path to defend an accused. A teacher might be guided in how to present a given topic to a child of a given age, intellect or disability with multiple iterative approaches.
  To assist users to prepare for specific examinations, from organic chemistry to GED, SAT, GRE, to the bar exam.
  To provide users a subscription or purchase service where downloads are purchased separately, in blocks, or for a period of time—much as music and other entertainment is.
  To guide users in how to operate within the law or established rules, and avoid hurtful, risky, and ill-advised actions within guidelines of society, a company, or other organization.
  To suggest alternatives based on information gathered periodically or continuously about a decision's, individual's, or goal's environment once the decision process has begun.
  To assist users to re-mediate and potentially recover from past decisions.
  To collect a history of an individual's behavior and suggest critical improvements.

To assist users in the operation of machinery, vehicles, and complex systems.

To provide an information system for a particular product or service. For example, an online medical records and patient care management system that is accessible form any connected terminal. It may act differently depending on the users role (patient, doctor, therapist, care giver, care payer, etc).

To provide a life management plan which may use ESNs to define short term or long term paths to goals.

The hexagonal GUI can also be adjustable to an individual's given or measured personality attributes (risk taking, honesty, intuitiveness-creativity assertiveness, and the like) and aptitudes (physical prowess and coordination, intelligence, musical ability, technical talent, language articulation, and the like) or limitations (handicaps, learning disabilities, emotional and perceptional difficulties).

operate in response to delays in accessibility, such that some decisions are, delayed, made on time, last minute, recovered, reversed or made in preemptive ways— depending on the nature of the decision.

Basically, the hexagonal GUI of the various embodiments can be utilized as an interface for various types of information systems, guidance tools, and self-help tools where portability and compactness of the interface enhance or enable individual decisions or coordination of individual decisions.

Figure 20:
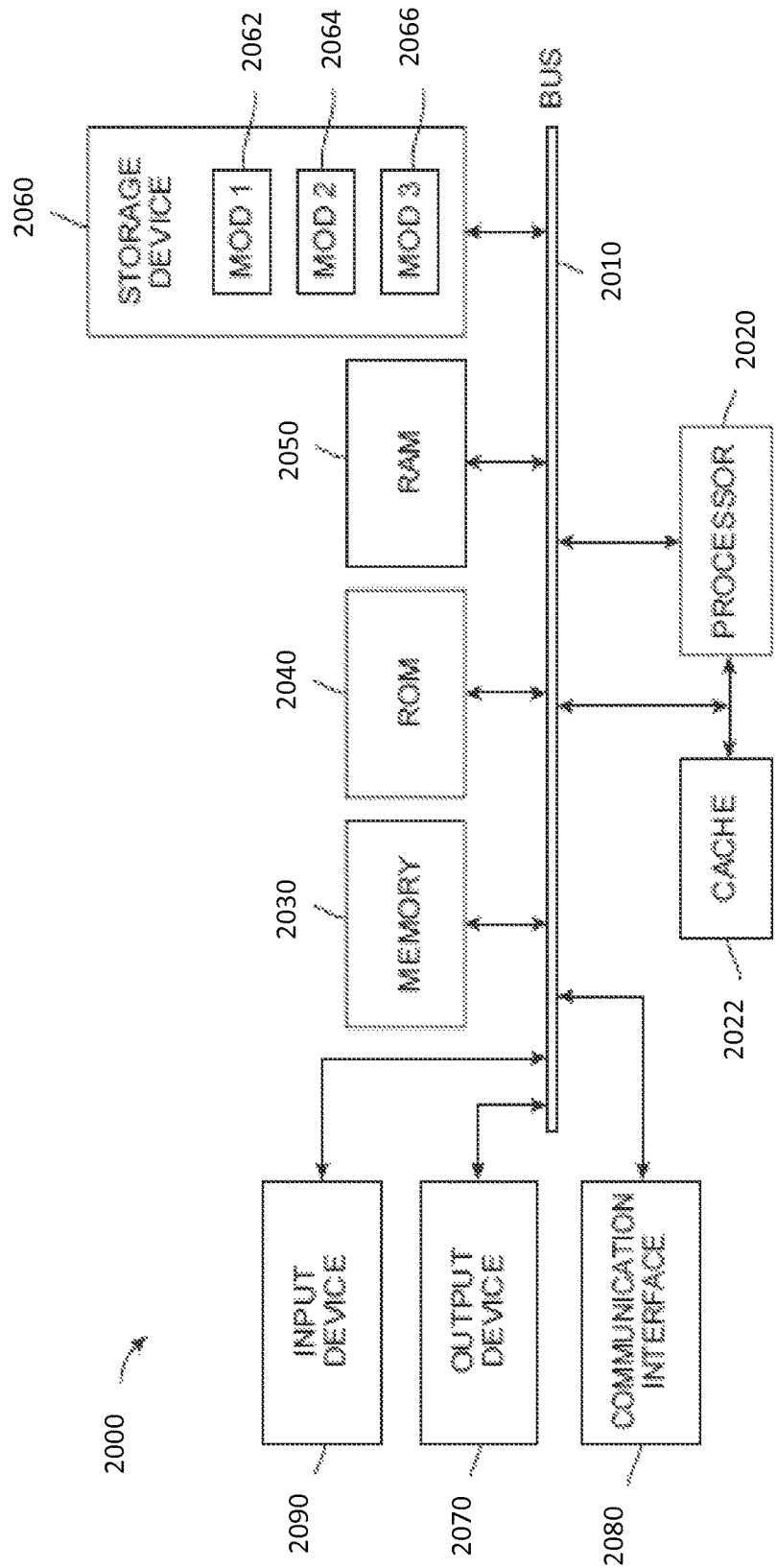
FIG. 20 shows an exemplary computer system for carrying out one or more of the various embodiments.

FIG. 20 illustrates an exemplary system 2000 that includes a general-purpose computing device 2000, including a processing unit (CPU or processor) 2020 and a system bus 2010 that couples various system components including the system memory 2030 such as read only memory (ROM) 2040 and random access memory (RAM) 2050 to the processor 2020. The system 2000 can include a cache 2022 of high speed memory connected directly with, in close proximity to, or integrated as part of the processor 2020. The system 2000 copies data from the memory 2030 and/or the storage device 2060 to the cache 2022 for quick access by the processor 2020. In this way, the cache 2022 provides a performance boost that avoids processor 2020 delays while waiting for data. These and other modules can control or be configured to control the processor 2020 to perform various actions. Other system memory 2030 may be available for use as well. The memory 2030 can include multiple different types of memory with different performance characteristics. It can be appreciated that the disclosure may operate on a computing device 2000 with more than one processor 2020 or on a group or cluster of computing devices networked together to provide greater processing capability. The processor 2020 can include any general purpose processor and a hardware module or software module, such as module 20 2062, module 2 2064, and module 3 2066 stored in storage device 2060, configured to control the processor 2020 as well as a special-purpose processor where software instructions are incorporated into the actual processor design. The processor 2020 may essentially be a completely self-contained computing system, containing multiple cores or processors, a bus, memory controller, cache, etc. A multi-core processor may be symmetric or asymmetric.

The system bus 2010 may be any of several types of bus structures including a memory bus or memory controller, a peripheral bus, and a local bus using any of a variety of bus architectures. A basic input/output (BIOS) stored in ROM 2040 or the like, may provide the basic routine that helps to transfer information between elements within the computing device 2000, such as during start-up. The computing device 2000 further includes storage devices 2060 such as a hard disk drive, a magnetic disk drive, an optical disk drive, tape drive or the like. The storage device 2060 can include software modules 2062, 2064, 2066 for controlling the processor 2020. Other hardware or software modules are contemplated. The storage device 2060 is connected to the system bus 2010 by a drive interface. The drives and the associated computer readable storage media provide non-volatile storage of computer readable instructions, data structures, program modules and other data for the computing device 2000. In one aspect, a hardware module that performs a particular function includes the software component stored in a non-transitory computer-readable medium in connection with the necessary hardware components, such as the processor 2020, bus 2010, display 2070, and so forth, to carry out the function. The basic components are known to those of skill in the art and appropriate variations are contemplated depending on the type of device, such as whether the device 2000 is a small, handheld computing device, a desktop computer, or a computer server.

Although the exemplary embodiment described herein employs the hard disk 2060, it should be appreciated by those skilled in the art that other types of computer readable media which can store data that are accessible by a computer, such as magnetic cassettes, flash memory cards, digital versatile disks, cartridges, random access memories (RAMs) 2050, read only memory (ROM) 2040, a cable or wireless signal containing a bit stream and the like, may also be used in the exemplary operating environment. Non-transitory computer-readable storage media expressly exclude media such as energy, carrier signals, electromagnetic waves, and signals per se.

To enable user interaction with the computing device 2000, an input device 2090 represents any number of input mechanisms, such as a microphone for speech, a touch-sensitive screen for gesture or graphical input, keyboard, mouse, motion input, speech and so forth. An output device 2070 can also be one or more of a number of output mechanisms known to those of skill in the art. In some instances, multimodal systems enable a user to provide multiple types of input to communicate with the computing device 2000. The communications interface 2080 generally governs and manages the user input and system output. There is no restriction on operating on any particular hardware arrangement and therefore the basic features here may easily be substituted for improved hardware or firmware arrangements as they are developed.

For clarity of explanation, the illustrative system embodiment is presented as including individual functional blocks including functional blocks labeled as a "processor" or processor 2020. The functions these blocks represent may be provided through the use of either shared or dedicated hardware, including, but not limited to, hardware capable of executing software and hardware, such as a processor 2020, that is purpose-built to operate as an equivalent to software executing on a general purpose processor. For example, the functions of one or more processors presented in FIG. 20 may be provided by a single shared processor or multiple processors. (Use of the term "processor" should not be construed to refer exclusively to hardware capable of executing software.) Illustrative embodiments may include microprocessor and/or digital signal processor (DSP) hardware, read-only memory (ROM) 2040 for storing software performing the operations discussed below, and random access memory (RAM) 2050 for storing results. Very large scale integration (VLSI) hardware embodiments, as well as custom VLSI circuitry in combination with a general purpose DSP circuit, may also be provided.

The logical operations of the various embodiments are implemented as: (1) a sequence of computer implemented steps, operations, or procedures running on a programmable circuit within a general use computer, (2) a sequence of computer implemented steps, operations, or procedures running on a specific-use programmable circuit; and/or (3) interconnected machine modules or program engines within the programmable circuits. The system 2000 shown in FIG. 20 can practice all or part of the recited methods, can be a part of the recited systems, and/or can operate according to instructions in the recited non-transitory computer-readable storage media. Such logical operations can be implemented as modules configured to control the processor 2020 to perform particular functions according to the programming of the module. For example, FIG. 20 illustrates three modules Mod1 2062, Mod2 2064 and Mod3 2066 which are modules configured to control the processor 2020. These modules may be stored on the storage device 2060 and loaded into RAM 2050 or memory 2030 at runtime or may be stored as would be known in the art in other computer-readable memory locations. It should be noted that the intelligence of a system may be distributed over multiple connected systems, or be local as shown, or be remote to a connected terminal interface, or any combination.

Figure 21:
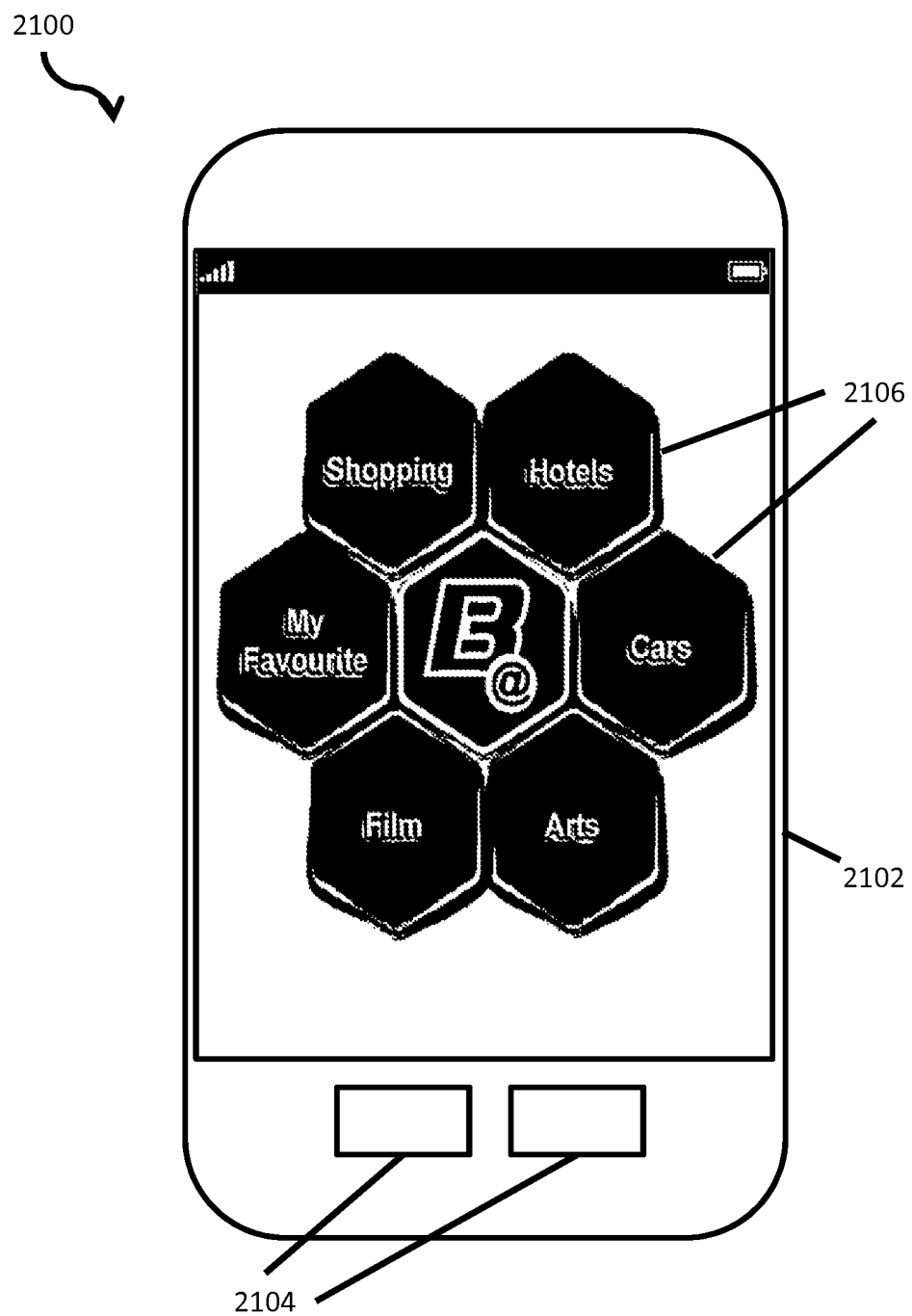
FIG. 21 shows an exemplary configuration of the hexagonal GUI of the various embodiments in a display of a computing device.

FIG. 21 shows an exemplary configuration of the hexagonal GUI of the various embodiments in a display of a computing device 2100. In the configuration of FIG. 21, computing device 2100 is configured as a mobile device or other hand held personal information device. In FIG. 21, device 2100 is illustrated with a display 2102 and controls 2104. The display 2102 can be configured as a touch screen display to allow a user to directly select from the hexagonal tiles 2106 in a hexagonal tiling (hextille arrangement) defining a hexagonal GUI to navigate through the hexagonal GUI as described above. However, alternatively or in combination with the touchscreen of display 2102, controls 2104 (or external control devices attached to mobile device 2100) can be used to navigate the hexagonal GUI defined by hexagonal tiles 2106.

While various embodiments of the present invention have been described above, it should be understood that they have been presented by way of example only, and not limitation. Numerous changes to the disclosed embodiments can be made in accordance with the disclosure herein without departing from the spirit or scope of the invention. Thus, the breadth and scope of the present invention should not be limited by any of the above described embodiments. Rather, the scope of the invention should be defined in accordance with the following claims and their equivalents.

Although the invention has been illustrated and described with respect to one or more implementations, equivalent alterations and modifications will occur to others skilled in the art upon the reading and understanding of this specification and the annexed drawings. In addition, while a particular feature of the invention may have been disclosed with respect to only one of several implementations, such feature may be combined with one or more other features of the other implementations as may be desired and advantageous for any given or particular application.

The terminology used herein is for the purpose of describing particular embodiments only and is not intended to be limiting of the invention. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

What is claimed is:

1. A method comprising:

providing a user interface comprising one or more primary icons, each of the one or more primary icons includes a hexagon and represents an initial state;

receiving user input selecting an inner portion of a first icon from the one or more primary icons;

responsive to selecting the inner portion of the first icon, displaying one or more secondary icons, each of the secondary icons includes a hexagon and positioned in the user interface in a hextille arrangement with respect to at least one of the first icon or another one of the secondary icons, wherein each of the secondary icons represents additional states subsequent to the initial state along valid paths from the initial state;

wherein displaying the one or more secondary icons further comprises determining whether any of the one or more secondary icons are associated with a first predetermined path from the first icon and altering an appearance of each of the one or more secondary icons by providing a tactile response with a tactile indicia based on the first predetermined path from the first icon;

receiving user input selecting an edge of a second icon from the one or more secondary icons; and responsive to selecting the edge of the second icon from the secondary icons, displaying one or more tertiary icons, each of the tertiary icons includes a hexagon and positioned in the user interface in a hextille arrangement with respect to at least one of the first icon, the second icon, or another one of the tertiary icons, wherein each of the tertiary icons represents further states subsequent to the additional state of the second icon along valid paths from the initial state and through the additional state of the second icon;

wherein displaying the one or more tertiary icons further comprises determining whether any of the one or more secondary icons are associated with a second predetermined path from the second icon and altering an appearance of each of the one or more tertiary icons by providing a tactile response with a tactile indicia based on the second predetermined path from the second icon.

2. The method of claim 1, further comprising:

receiving user input selecting an inner portion of the second icon from the one or more secondary icons; and responsive to selecting the inner portion of the second icon, terminating the displaying of any of the secondary icons not associated with valid paths associated with one of the additional states associated with the second icon and displaying the one or more tertiary icons in the hextille arrangement with respect to at least one of the first icon, the second icon, or another one of the tertiary icons.

3. The method of claim 1, further comprising:
during the displaying of the tertiary icons, detecting a sliding from the edge towards a one of the tertiary icons; and
responsive to the sliding of the edge towards the one of the tertiary icons, removing any of the secondary icons not associated with valid paths associated with a one of the additional states associated with the second icon and displaying the one or more tertiary icons during and after the sliding.

4. The method of claim 1, further comprising:
responsive to a tapping of the first icon, causing an altering of at least one of the secondary icons.

5. The method of claim 1, further comprising:
responsive to a tapping of the first icon, causing an altering of the first icon.

6. The method of claim 1, further comprising:
responsive to a tapping of an edge or vertex between adjacent icons, causing an altering of at least one of the adjacent icons.

7. A system, comprising:
a display;
a processor communicatively coupled to the display; and
a computer-readable medium, having stored thereon a computer program comprising a plurality of code sections, the plurality of code sections configured for causing the processor to perform the steps of:
providing a user interface on the display comprising one or more primary icons, each of the one or more primary icons includes a hexagon and represents an initial state;
receiving user input selecting a first icon from the one or more primary icons;
responsive to selecting the inner portion of the first icon, displaying one or more secondary icons on the display, each of the secondary icons includes a hexagon and positioned in the user interface in a hextille arrangement with respect to at least one of the first icon or another one of the secondary icons, wherein each of the secondary icons represents additional states subsequent to the initial state along valid paths from the initial state;
wherein displaying the one or more secondary icons further comprises determining whether any of the one or more secondary icons are associated with a first predetermined path from the first icon and altering an appearance of each of the one or more secondary icons by providing a tactile response with a tactile indicia based on the first predetermined path from the first icon;
receiving user input selecting an edge of a second icon from the one or more secondary icons; and
responsive to selecting the edge of the second icon from the one or more secondary icons, displaying one or more tertiary icons on the display, each of the tertiary icons includes a hexagon and positioned in the user interface in a hextille arrangement with respect to at least one of the first icon, the second icon, or another one of the tertiary icons, wherein each of the tertiary icons represents further states subsequent to the additional state of the second icon along valid paths from the initial state and through the additional state of the second icon;
wherein displaying the one or more tertiary icons further comprises determining whether any of the one or more secondary icons are associated with a second predetermined path from the second icon and altering an appearance of each of the one or more tertiary icons by providing a tactile response with a tactile indicia based on the second predetermined path from the second icon.

8. The system of claim 7, further comprising code sections configured for causing the processor to perform the step of:
receiving user input selecting an inner portion of the second icon from the one or more secondary icons; and
responsive to selecting the inner portion of the second icon, removing from the display any of the one or more secondary icons not associated with valid paths associated with one of the additional states associated with the second icon and displaying the one or more tertiary icons in the hextille arrangement with respect to at least one of the first icon, the second icon, or another one of the tertiary icons.

9. The system of claim 7, further comprising code sections configured for causing the processor to perform the step of:
during the displaying of the tertiary icons, detecting a sliding from the one of the edges towards a one of the tertiary icons; and
responsive to the sliding of the one of the edges towards a one of the tertiary icons, removing from the display any of the secondary icons not associated with valid paths associated with a one of the additional states associated with the second icon and displaying the one or more tertiary icons during and after the sliding.

10. The system of claim 7, further comprising code sections configured for causing the processor to perform the step of:
responsive to a tapping of the first icon, causing an altering of at least one of the secondary icons on the display.

11. The system of claim 7, further comprising code sections configured for causing the processor to perform the step of:
responsive to a tapping of the first icon, causing an altering of the first icon on the display.

12. The system of claim 7, further comprising code sections configured for causing the processor to perform the step of:
responsive to a tapping of an edge or vertex between adjacent icons, causing an altering of at least one of the adjacent icons on the display.

13. A computer-readable medium having stored thereon a plurality of code sections configured for causing a computing device to present a graphical user interface, the plurality of code sections configured for causing the computing device to perform the steps of:
providing a user interface comprising one or more primary icons, each of the one or more primary icons includes a hexagon and represents an initial state;
receiving user input selecting an inner portion of a first icon from the one or more primary icons;
responsive to selecting the inner portion of the first icon, displaying one or more secondary icons, each of the secondary icons includes a hexagon and positioned in the user interface in a hextille arrangement with respect to at least one of the first icon or another one of the secondary icons, wherein each of the secondary icons represents additional states subsequent to the initial state along valid paths from the initial state;
wherein displaying the one or more secondary icons further comprises determining whether any of the one or more secondary icons are associated with a first predetermined path from the first icon and altering an appearance of each of the one or more secondary icons by providing a tactile response with a tactile indicia based on the first predetermined path from the first icon;

receiving user input selecting an edge of a second icon from the one or more secondary icons; and responsive to selecting the edge of the second icon from the secondary icons, displaying one or more tertiary icons on, wherein each of the tertiary icons includes a hexagon and positioned in the user interface in a hextille arrangement with respect to at least one of the first icon, the second icon, or another one of the tertiary icons, wherein each of the tertiary icons represents further states subsequent to the additional state of the second icon along valid paths from the initial state and through the additional state of the second icon;

wherein displaying the one or more tertiary icons further comprises determining whether any of the one or more secondary icons are associated with a second predetermined path from the second icon and altering an appearance of each of the one or more tertiary icons by providing a tactile response with a tactile indicia based on the second predetermined path from the second icon.

14. The computer-readable medium of claim 13, further comprising code sections configured for causing the computing device to perform the step of:

receiving user input selecting an inner portion of the second icon from the one or more secondary icons; and responsive to selecting the inner portion of the second icon, terminating the displaying of any of the secondary icons not associated with valid paths associated with one of the additional states associated with the second icon and displaying the one or more tertiary icons in the hextille arrangement with respect to at least one of the first icon, the second icon, or another one of the tertiary icons.

15. The computer-readable medium of claim 13, further comprising code sections configured for causing the computing device to perform the step of:

responsive to a tapping of the first icon, causing an altering of at least one of the secondary icons in the user interface.

16. The computer-readable medium of claim 13, further comprising code sections configured for causing the computing device to perform the step of:

responsive to a tapping of the first icon, causing an altering of the first icon in the user interface.

17. The computer-readable medium of claim 13, further comprising code sections configured for causing the computing device to perform the step of:

responsive to a tapping of an edge or vertex between adjacent icons, causing an altering of at least one of the adjacent icons in the user interface.

* * * * *